United States Patent [19]
Reynolds

[11] Patent Number: 5,152,175
[45] Date of Patent: Oct. 6, 1992

[54] BUBBLE MEASUREMENT CELL

[75] Inventor: Vaughan G. Reynolds, Nepean, Canada

[73] Assignee: Her Majesty the Queen in right of Canada as represented by the Minister of Energy, Mines & Resources, Canada

[21] Appl. No.: 613,242

[22] Filed: Nov. 14, 1990

[51] Int. Cl.⁵ .................................... G01N 15/02
[52] U.S. Cl. ................... 73/19.01; 73/865.5
[58] Field of Search ............... 73/19.01, 19.03, 53, 73/865.5

[56] References Cited

U.S. PATENT DOCUMENTS

| | | | |
|---|---|---|---|
| 3,240,674 | 3/1966 | Ledwidge | 73/19.03 X |
| 3,381,525 | 5/1968 | Kartluke et al. | 73/53 X |
| 3,529,234 | 9/1970 | Keen | 73/19.03 X |
| 3,622,958 | 11/1971 | Tucker et al. | 73/19.03 X |
| 3,738,154 | 6/1973 | Henry | 73/19.07 |
| 4,418,565 | 12/1983 | St. John | 73/19.03 |
| 4,763,525 | 8/1988 | Cobb | 73/19.03 X |
| 4,862,729 | 9/1989 | Toda et al. | 73/19.05 |

*Primary Examiner*—Hezron E. Williams
*Assistant Examiner*—Joseph W. Roskos
*Attorney, Agent, or Firm*—Louis Weinstein

[57] ABSTRACT

A bubble measurement cell is provided for measuring size distribution of gas bubbles in a liquid. The bubble measurement cell is adapted for insertion in a flotation column having a transparent, vertically-oriented, bubble-viewing window. The bubble measurement cell includes an antechamber, for placement adjacent the window in the flotation column, the antechamber having a transparent rear face. The transparent bubble-viewing window and the transparent rear face allow light to enter in sufficient quantity to illuminate the bubbles enabling photographic imaging thereof. A forward, downwardly-pointing deflection wedge deflects upwardly-moving bubbles. A transparent viewing chamber is provided which is situated to the rear of the antechamber and which includes a rear face, a transparent front face spaced from the rear face, and a pair of inner, vertical lateral spacers. The transparent viewing chamber is bounded at its bottom by a pair of inner, transversely-running, wedges forming a narrow inlet, which leads to a region of the viewing chamber of larger cross-sectional area by being thicker and wider than the thickness and the width of the inlet. An outlet is provided at the upper end of the viewing chamber to permit the escape of gas bubbles. In use, a monolayer of bubbles is presented in the transparent viewing chamber for the taking of a photograph of the shadows of the bubbles. Such photograph can be subjected to photographic analysis to measure the size and the distribution of the bubbles.

14 Claims, 4 Drawing Sheets

BUBBLE MEASUREMENT CELL

BACKGROUND OF THE INVENTION (i) Field of the Invention

This invention relates to a bubble measurement cell, and to a method for measuring size distribution of gas bubbles in a liquid.

(ii) Description of the Prior Art

In column flotation, there are numerous ways of generating bubbles. However, knowledge of the size distribution of gas bubbles in a liquid produced is critical in assessing the relative merits of bubble generators and in investigations into the mechanics of the flotation procedure. The need, therefore, is to measure size distribution of gas bubbles in a liquid in a lamella of known dimensions located within the flotation column, close to, but away from, the walls of the flotation column.

Techniques for determining the presence or absence of gas bubbles in liquids are known. Apparatus for determining the onset of the formation of bubbles, i.e., cavitation or boiling, but not the proportion of bubbles, have been described by a number of patentees.

In U.S. Pat. No. 3,381,525 to Kartluke et al., sound waves were launched into a liquid. The liquid was monitored for sound waves at subharmonic frequencies of the launched sound waves. When subharmonic waves were detected, cavitation is imminent or has begun.

In U.S. Pat. No. 3,240,674 to Ledwidge, a similar technique was used. No sound waves were added to the liquid. Instead, the frequencies of sound waves in the liquid were monitored for a selected spectrum peak that indicated localized boiling, a prelude to boiling of the entire liquid volume.

U.S. Pat. No. 3,622,958 to Tucker et al, disclosed a number of methods of detecting the existence of gas bubbles in a liquid. Waves at a fundamental frequency were launched into a liquid by a first transducer and waves at harmonic frequencies are detected by a second transducer. Detection of harmonic frequency signals indicated the presence of gas bubbles. Alternatively, reflected waves at harmonic frequencies were detected by the same transducer that launches the fundamental frequency wave. In still another embodiment, multiple frequency sound waves were launched into the liquid which was monitored for waves having frequencies equal to a sum or difference of two of the frequencies of the launched waves.

Many other patents purport to provide a solution to the problem of measurement of the size distribution of gas bubbles in a liquid.

U.S. Pat. No. 3,529,234 patented Sep. 15, 1970 to R. D. Keen, provided a method and apparatus for solving the problem of detecting bubbles or vapor within the liquid metal system or liquid metal droplets within a vapor system. The patentee used a high frequency oscillator which was placed adjacent the pipe containing the flowing liquid or vapor. An oscillator was tuned for resonance coupling at the characteristic resonance absorption frequency of the liquid. Energy absorption by the liquid was indicated by either the oscillator current measurement or by a sensor coil or antenna which is connected to a detector or radio receiver. The receiver or oscillator current measurement, when calibrated, indicated discrete vapor or bubble count in a liquid metal system or the percentage of liquid-vapor flow, vapor quality in a vapor system. Bubbles were also detected, and the size of bubbles can be determined. The tank coil of a high frequency oscillator was placed about a pipe containing the flowing fluid which may be in either a liquid or vapor phase or combination thereof. At a particular frequency, resonance coupling occurred between the coil and the nuclei of the fluid, resulting in an absorption of energy by the nuclei. The amount of energy absorption depended upon the cross sectional area of the fluid as modified by any vapor bubbles, so that the output from a detecting circuit indicated the bubble content of a liquid fluid system or the vapor quality or amount of liquid in a vapor system.

U.S. Pat. No. 3,738,154 patented Jun. 12, 1973 to R. E. Henry, provided a method of measuring entrained gas in a liquid. In the patented method, a choked converging-diverging nozzle was employed in a method of detecting the presence, and measuring the volumetric concentration, of entrained gas in a liquid. The liquid-gas mixture was accelerated through the nozzle to critical flow conditions and the pressure at the throat of the nozzle was measured. The temperature and pressure of the mixture of the stagnation region were monitored, the throat pressure of the liquid-gas mixture being a function of only the void fraction at any given stagnation temperature and pressure.

U.S. Pat. No. 4,418,565 patented Dec. 6, 1983 by P. A. St. John, provided an ultrasonic bubble detector. In the patented device, the ultrasonic bubble detection apparatus utilized a typically one-piece, rigid housing having a channel defined therein for receiving flow tubing in which bubbles were to be detected. First and second ultrasonic sending and receiving transducers were positioned on opposite sides of the channel, with an aperture communicating between each of the transducers and the channel, the aperture being filled with an elastomeric material capable of transmitting ultrasound energy between the channel and each transducer means. An air-containing slot was positioned at the bottom of the channel to hinder the propagation of ultrasound energy through the housing from the first to the second transducer by a route other than one passing through the elastomeric material.

U.S. Pat. No. 4,763,525 patented Aug. 16, 1988 to W. N. Cobb, provided apparatus and method for determining the quantity of gas bubbles in a liquid. In the patented method, an ultrasonic wave was launched into the mixture and magnitudes of two reflected waves were measured, and compared. The logarithm of the magnitudes of the reflected waves was a measure of the quantity of gas content.

U.S. Pat. No. 4,862,729 patented Sep. 5, 1989 by K. Toda et al, provided a method for measuring the amount of the gas contained in liquid. The patented method included introducing a liquid material into a vacuum measuring chamber, changing the volume of the measuring chamber to provide two different liquid pressures of the liquid material in the measuring chamber, and detecting the different pressures to measure the amount of gas on the basis of Boyle's law.

Thus, as pointed out above, the known technology does not provide a simple, reliable method of quantitatively measuring the bubble content of a liquid-gas mixture. In order to avoid the problem of direct measurements, the prior art has relied instead on secondary, indirect measurements, assumptions, and calculations (e.g., using known rates of air injection, known water volume, etc.), and assuming no (or some fractional rate of) coalescence of bubbles.

In a photographic system for directly measuring the size distribution of gas bubbles in a liquid, the main limitation is the photographic process required for recording and analysis; the film known by the Trade-mark KODACHROME film now in use requires five working days for processing. Also, even though the image analysis process now in use works quite well, it needs some refinement to provide optimum results.

SUMMARY OF THE INVENTION (i) Aims of the Invention

It is an object, therefore, of one broad aspect of the present invention to provide a cell for the direct measurement of the size distribution of gas bubbles in a liquid.

Another object of this invention is to provide a method for detecting the presence, and for measuring the volumetric concentration, of entrained gas in a liquid.

(ii) Statement of Invention

This invention provides a bubble measurement cell for measuring the size distribution of gas bubbles in a liquid by isolating the bubbles in situ from a high volume of bubbles without modifying the bubbles in any way, the bubble measurement cell being adapted for insertion in a flotation column having a transparent, vertically-oriented, bubble-viewing window therein, the bubble measurement cell comprising: an antechamber, for placement adjacent the window in the flotation column, the antechamber being provided with a transparent rear face, the transparent bubble-viewing window and the transparent rear face being provided for the purpose of allowing light to enter in sufficient quantity to illuminate the bubbles and to enable photographic imaging thereof, and a forward, downwardly-pointing deflection wedge to deflect upwardly-moving bubbles; a transparent viewing chamber, the transparent viewing chamber being situated to the rear of the antechamber, the transparent viewing chamber including a rear face, a transparent front face spaced from the rear face, and a pair of inner, vertical, lateral spacers, the transparent viewing chamber being bounded at its bottom by a pair of inner, transversely-running, wedges, the wedges thereby providing a narrow inlet, the narrow inlet leading to a region of the viewing chamber which is a region of larger cross-sectional area by being thicker and wider than the thickness and the width of the inlet; and means at the upper end of the viewing chamber to permit the escape of gas bubbles; whereby a monolayer of the bubbles is presented in the transparent viewing chamber for the taking of a photograph of the shadows of those bubbles, the photograph of the shadows being adapted to be subjected to photographic analysis for the measurement of size distribution.

This invention also provides a method for analyzing the size distribution of gas bubbles in a liquid within a vertically-oriented chamber which method comprises: providing a vertically-oriented, transparent window in the vertically-oriented chamber to enable the viewing of an upwardly-moving, turbulent stream of gas bubbles; providing a transparent viewing zone spaced from the transparent window, the transparent viewing zone being situated within the vertically-oriented chamber and also being situated within the upwardly-moving, turbulent stream of gas bubbles; streaming the gas bubbles upwardly through a narrow rectangular opening into the transparent viewing zone, whereby the gas bubbles are formed into a moving monolayer of bubbles which move upwardly in laminar flow; and moving lateral bubbles which are adjacent to the transparent viewing zone laterally away from the transparent viewing zone, whereby to separate the bubbles from the previously described monolayer of bubbles moving upwardly in laminar flow, the laterally-moved bubbles being thereby permitted to flow upwardly substantially unimpeded; whereby there is a minimum of disturbance of the gas bubbles in the transparent viewing zone before and while the bubbles are presented for viewing; taking a photograph of the shadows of these bubbles; and then analyzing the photograph of the shadows of the bubbles to measure the size and the distribution of the bubbles.

This invention also provides an attachment for a particle size analyzer, the particle size analyzer comprising: a U-shaped bracket for mounting adjacent a sample well; a photographic slide holder secured to the forward arm of the U-shaped bracket, the slide holder including a pair of downwardly projecting legs, each leg being provided with means for holding a photographic slide within the sample well; and means mounted on the forward arm of the U-shaped bracket for permitting horizontal and vertical movement of the photographic slide.

(iii) Other Features of the Invention

In one feature of the bubble measurement, the photographic analysis is preferably carried out by the introduction of the photograph to a semi-automated, computerized particle size analyzer having image analysis capabilities, whereby photographic images of shadows of the bubbles are treated as particles by the analyzer, the analyzer generating size distribution data relating to the shadows of the bubbles.

In one feature of such cell, the rear face of the antechamber and the front face of the viewing chamber are preferably the same face. The inlet is a narrow rectangular inlet which is preferably adjustable in width, e.g., where the adjustable width is provided by a pair of laterally-movable gap adjusters.

In another feature of such cell the viewing chamber preferably is provided with a pair of converging lower edges to provide a truncated knife edge. The slot-like inlet includes a pair of spaced-apart knife-edge wedges. The cell preferably includes a scale in association with the transparent viewing chamber to enable direct measurement of the size and distribution of the gas bubbles by comparison of the photographic image of the shadows of the bubbles with the photographic image of the scale. The rear face of the viewing chamber preferably is provided with a white face, the white-face providing improved contrast for the photographing of the shadows of the bubbles.

In another feature of such cell, a gasket is preferably provided around the periphery of the forwardly-projecting frame of the antechamber where it contacts the transparent bubble-viewing, vertically-oriented window.

In one feature of the method of this invention, the analysis of the photographic images of the shadows of the bubbles, the shadows are treated as particles by the analyzer, which then generates size distribution data determined from the shadows of the bubbles.

In another feature of the method of the invention, the method preferably includes the step of passing the upwardly-moving stream through a narrow rectangular zone to the transparent viewing zone the transparent viewing zone being of larger cross-sectional area, thereby to reduce the likelihood of coalescence, to reduce the adherence of bubbles to the wall of the vertically-oriented chamber and the transparent viewing chamber and to enhance bubble shadow definition in a photograph.

(iv) Generalized Description of the Invention

The invention thus provides a simple method and apparatus for measuring the size distribution of gas bubbles in a liquid. The present invention provides a small sampling cell which allows the photographing in situ of a lamella which is situated within the interior of a bubble tank, but away from the walls of the bubble tank, the lamella containing air bubbles. A scale is preferably incorporated so that bubbles may be measured directly by comparison with the scale, or by using image analysis software (and a specially-constructed adapter) on a particle size analyzer known by the trademark BRINKMANN.

BRIEF DESCRIPTION OF THE DRAWINGS

In the accompanying drawings.

Figure 1:
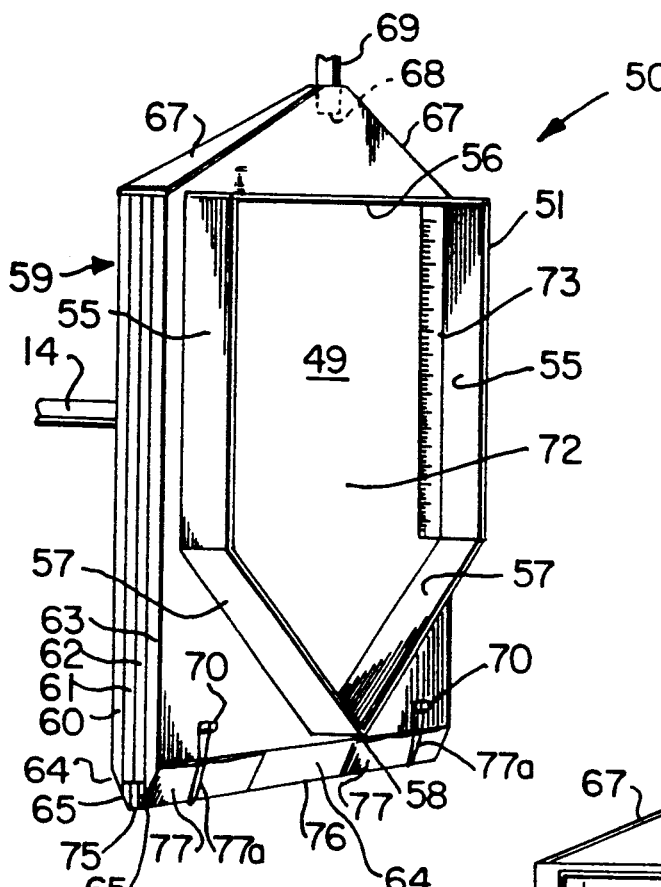
FIG. 1 is a perspective view of a bubble measurement cell of one embodiment of this invention.
Figure 2:
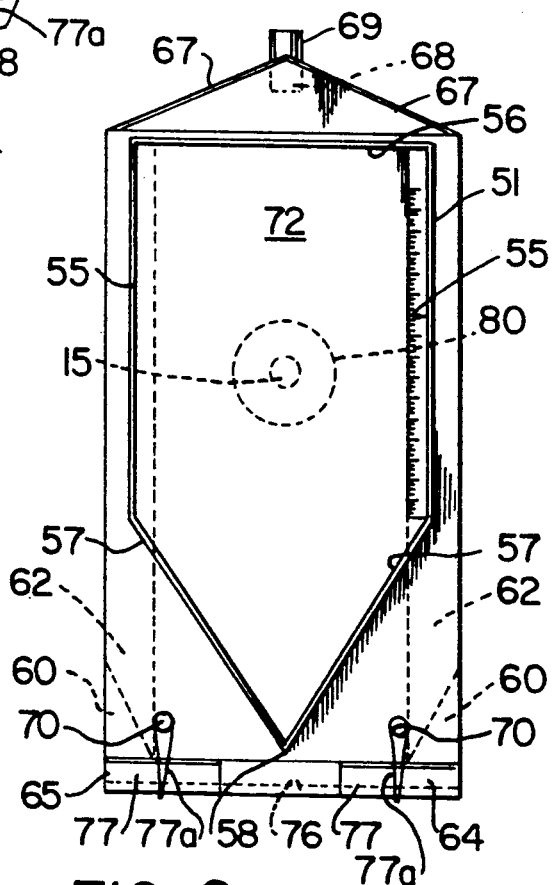
FIG. 2 is a front view of the bubble measurement cell of FIG. 1.
Figure 3:
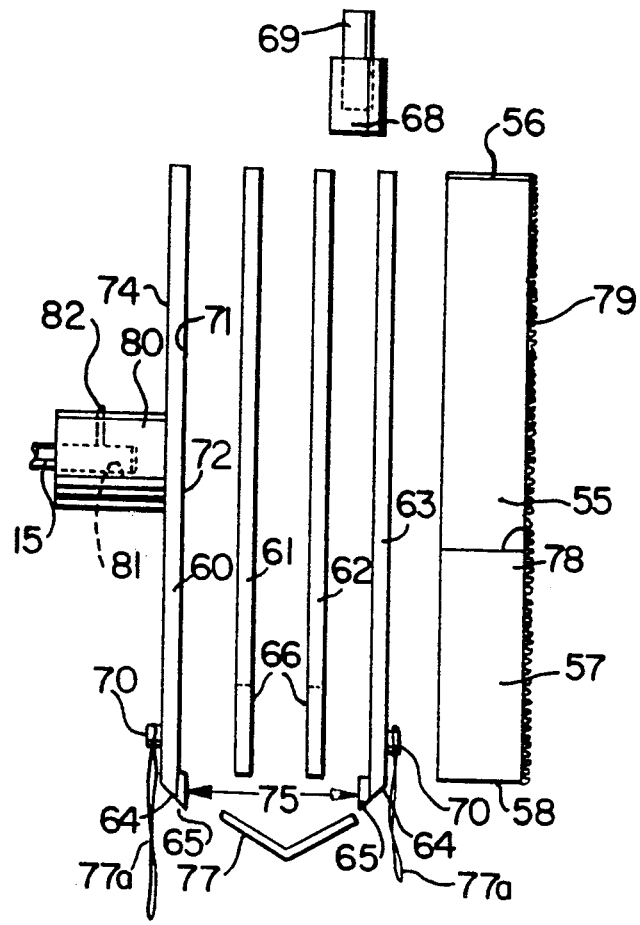
FIG. 3 is an exploded side-elevational view of the bubble measurement cell of FIG. 1.

DESCRIPTION OF PREFERRED EMBODIMENTS (i) Description of FIGS. 1, 2 and 3

As seen in FIGS. 1, 2 and 3, the bubble measurement cell 50 includes a generally-rectangular frame 51 comprising a pair of spaced-apart vertical walls 55, an upper roof 56 and a pair of converging floors 57 meeting at a V-point 58 to provide an antechamber 49. The antechamber 49 provides a front face for a laminated viewing chamber 59 provided by two large outer sheets 60 and 63 (at least sheet 63 being transparent), and two inner lateral vertical spacer sheets 61, 62 at each lateral edge of sheets 60 and 63, the sheets being formed, e.g., of acrylic platic. The inner lateral spacer sheets 61, 62 are each provided with tapered lower edges 66. Outer sheets 60, 63 are each provided with an outer, lower, upwardly tapered face 64. Outer sheets 60, 63 are each provided with an inner, transversely-extending, knife-edge bubble-aperture guide 65.

The laminated viewing chamber 59 is thus a rectangular parallelepiped chamber provided by outer sheets 60, 63 and inner lateral vertical spacer sheets 61, 62. The gap 75 between bubble aperture guides 65 provides a rectangular entrance aperture or inlet to the viewing chamber 59 at the truncated knife edges 64 of the outer sheets 60, 63. The width of the inlet 75 is adjustable by means of a pair of laterally-movable gap adjusters 77 which are each transversely slidable. The gap adjusters 77 may be held in place by alternative means well-known to those skilled in the art. For example, the lower edge of each of outer sheets 60, 63 may be provided with horizontally-extending grooves, within which upper inturned edges of the gap adjusters 77 are fitted and held. Alternatively, elastically-expandable spring means 77a may be hooked around retainer tabs 70 on the outer faces of each of outer sheets 60, 63.

The laminated viewing chamber 59 terminates in an upper converging gabled roof 67, provided with a bubble vent header 68 terminating in a bubble vent line 69.

The interior rear face 71 of the rear sheet 60 is provided with an opaque white background 72. Superposed on one edge of the white background 72 is a scale 73. The rear face 74 of the sheet 60 is provided with a mounting dowel 80, e.g., of acrylic plastic. The horizontal support rod 15 is fitted into a well 81 within mounting dowel 80 and is secured therein by means of a set screw 82. The front face of sheet 63 provides a rear face for the antechamber 49.

The front face 78 of the generally-rectangular frame 51 is provided with a gasket material 79, e.g., of cotton rope, to provide a flexible seal and wiping action to clean the inside of window 53 of the bubble column 20. (See FIG. 6).

The generally-rectangular frame 51 of the bubble measurement cell 50 is in contact with window 53 of the column 20. The bubbles in the viewing chamber 59, which are visible through transparent sheet 63, are seen in the window 53 of the column 20, and are then photographed.

Figure 4:
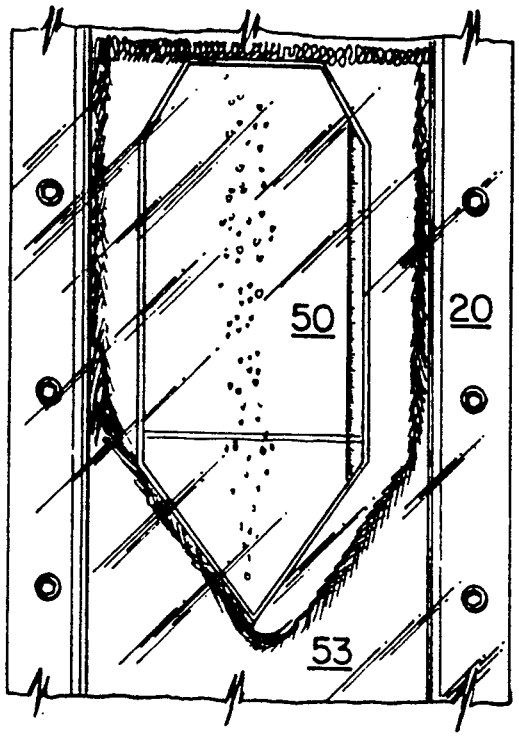
FIG. 4 is a drawing of an actual photograph of the bubble measurement cell of FIG. 1 mounted within a bubble column, and in actual use.

(ii) Description of FIG. 4

FIG. 4 is a drawing of an actual photograph of the window 53 of the column 20 with the bubble measurement cell 50 and bubbles therein, during use.

Figure 5:
FIG. 5 is a reproduction of a computer-generated printout of a computer generated portion of the photograph shown in which FIG. 4 as produced by the BRINKMANN TM particle size analyzer.
Figure 7:
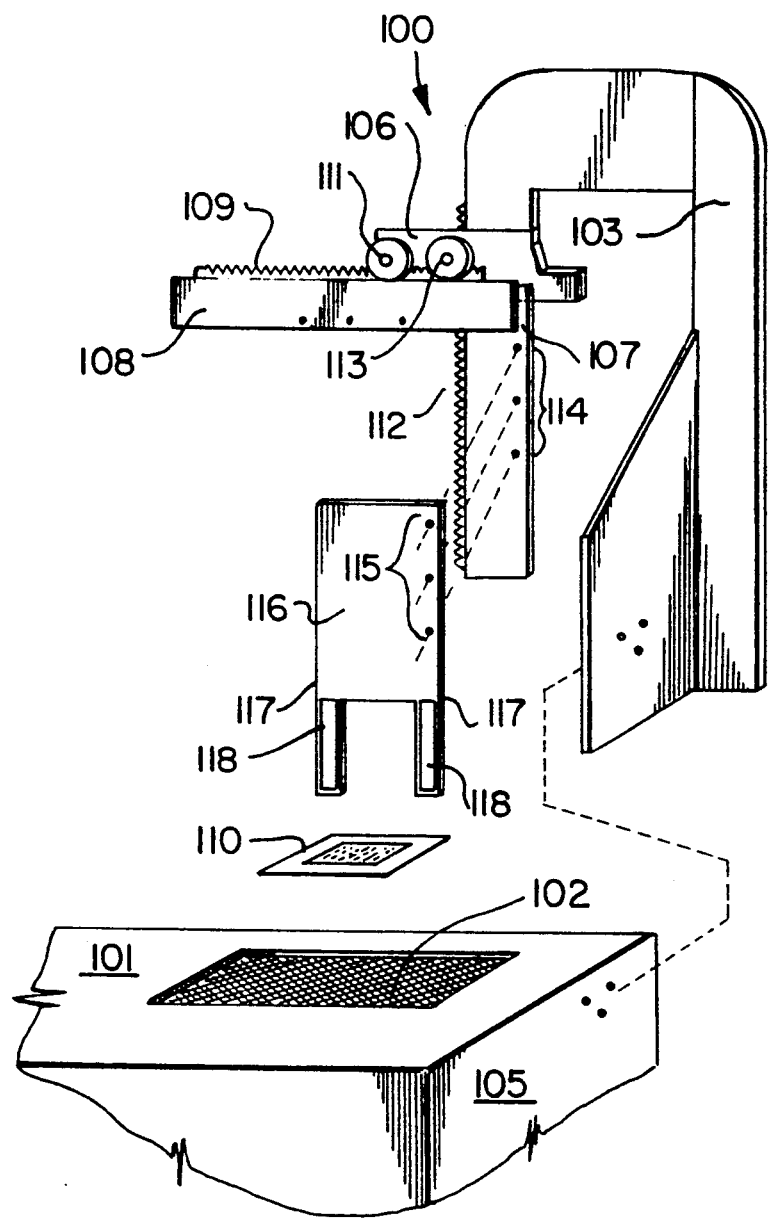
FIG. 7 is a side-elevational view of an adapter for attachment to a BRINKMANN TM particle size analyzer to analyze photographs provided by using the bubble measurement cell of an aspect of this invention.

(iii) Description of FIGS. 5 and 7

Photographic transparency slides developed therefrom are analyzed by means of a particle size analyzer 100 known by the Trade-mark BRINKMANN. (See FIG. 7). A copy of a printout of a bubble analysis on one such slide is shown in FIG. 5.

Figure 6:
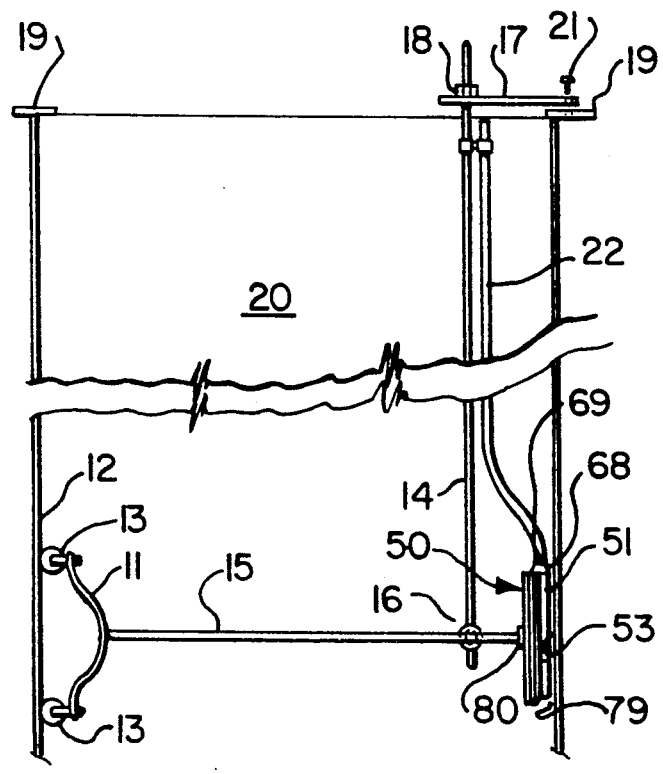
FIG. 6 shows one way of mounting the bubble measurement cell of FIG. 1 within the bubble column.

(iv) Description of FIG. 6

FIG. 6 shows the bubble measurement cell 50 within the column flotation tank 20, the size and distribution of gas bubbles within the liquid therein of which is to be determined. A horizontally-oriented support rod 15, e.g., of aluminum, is secured to the rear of the bubble measurement cell 50 namely to the rear face 74 of the rear sheet 60 by means of the mounting dowel 80 as previously described. The front of the bubble measurement cell 50 is open; it is provided by the generally-rectangular frame 51, with a V-shaped floor 57 secured to the front face of the front sheet 63. As previously described, the gasket material 79 on the front face 78 of the generally-rectangular frame 51 contacts the glass plate forming the vertical window 53 in the column 20. The horizontal rod 15 is secured to a sheet metal spring 11, e.g., of stainless steel and is movably held to the inner wall 12 of the column 20 by means of a pair of casters 13.

The horizontal rod 15 is secured to a vertically-oriented rod 14, e.g., by means of a suitable clamp 16, e.g., that known by the Trade-mark of FLEXAFRAME. The vertical rod 14 carries a support strap 17, e.g., of sheet iron, to which it is secured by suitable means, e.g., a thumbscrew 18. The top wall flange 19 of the column 20 secures the support strap 17 by suitable means, e.g., a thumb screw 21. An air bubble conducting tube 22, e.g., of plastic, is connected to the bubble vent line 69 of the bubble measurement cell 50.

(v) Description of FIG. 7

A slide mount adapter to enable bubble analysis is shown on FIG. 7. The BRINKMANN TM particle size analyzer 100 includes a generally-rectangular box 101, which includes a sample well 102. A U-shaped mounting bracket 103 is secured to a side wall 105 of the box 101 by conventional means. A movable slide mounting device 106 is secured to the outer arm 107 of the mounting bracket 103. Mounting device 106 is provided with a horizontal arm 108 in which a rack 109 is secured, so that horizontal adjustments may be made by the horizontal adjust knob 111. The outer arm 107 is provided with a vertical rack 112, so that vertical adjustments may be made by means of vertical adjust knob 113.

The outer arm 107 is provided with mounting means 114, e.g., tapped aperture, whereby cooperative mounting means 115, e.g., screws may secure a slide mount plate 116 to the outer arm 107. Plate 116 is provided with a pair of legs 117 upon each of which is double sided adhesive tape 118.

The photographic slide 110 is secured to the double-sided adhesive tape 118.

OPERATION OF PREFERRED EMBODIMENTS

In the use of the bubble measurement cell of an aspect of this invention, bubbles rising along the inner surface of the column window encounter a downward-pointing deflection wedge which moves all bubbles to the sides of the viewing area, where they continue to rise to the surface. Bubbles which are initially a little deeper (i.e., farther from the window) encounter a pair of long, narrow "stream-forming wedges" which run horizontally, at right angles to the first wedge, and parallel to the column window. These form an entrance aperture having a long and narrow rectangular cross section. The size of the inlet or entrance aperture is controlled by means of a pair of laterally-movable gap adjusters. Bubbles within this entrance area continue to rise unimpeded, while those outside the entrance area are deflected to the rear of the cell, i.e., to a zone within the column or to the front of the column where they are further deflected by the downwardly-pointing deflection wedge.

All of this "processing" of the bubbles is to ensure that there is an absolute minimum of disturbance of the bubbles in the column before they are presented for viewing or photographing (e.g., pressure is maintained at a constant value, the vertical rise path is unaltered, "crowding" or concentration of bubbles is avoided in order to minimize coalescence, etc.).

Bubbles rising a few millimeters above the entrance aperture enter a region of slightly larger cross-sectional area, namely into a viewing chamber which is wider and larger than the entrance aperture. This feature is designed: further to reduce the likelihood of coalescence; to reduce "wall effect" (the adherence of bubbles to the wall or their slower movement upwards because of their proximity to the wall); and to enhance bubble shadow definition in the photographs, by increasing the distance of each from the rear wall or "screen".

Hence, a viewer sees a thin lamella of bubbles within the column away from the window of the column. They rise just as they would in the "body" of the column but without most of the turbulence found there, and unobscured by bubbles which would have been in the space between the lamella and the window. (These have been removed from the viewing field by the "deflection wedge".) To ensure the absence of any bubbles in this area, a gasket is affixed around the periphery of the cell where it contacts the window,—even at the top, since small openings there allow the powerful turbulence present to carry small, slow-rising bubbles well into the viewing area.

For the same reason, the top of the viewing lamella must be enclosed, and bubbles conducted all the way to the surface by an independent path. Failure to do this results in ingress of bubble-laden water which flows downward through the cell and exits via the entrance aperture. This flow prevents the entrance of even a single bubble in the intended (upward) direction.

When frother levels and/or air flow rates are high, it is sometimes necessary to restrict the number of bubbles passing through the entrance aperture. This is easily accomplished with the "gap adjuster" slides. A central stream of bubbles is thus formed which spreads laterally somewhat as it rises, reducing bubble density. The clear regions at the sides of this stream further enhance shadow definition since the side illumination used tends to cast shadows where they are not obscured by foreground bubbles.

Even sophisticated available image analysis software cannot recognize a bubble as a round shape. In normal illumination, what is easily recognized visually as a sphere is seen by image analysis software as a collection of curved lines, some very dark and some very light, but not as a single round shape. However, bubble shadows are of uniform greyness, and almost perfectly round. These characteristics are well suited to image analysis software.

To enhance shadow definition and the separation of shadows from the bubbles causing them, the rear surface of the cell is preferably painted white, and the bubbles are preferably illuminated from the side using an ordinary electronic flash unit. As mentioned above, the positioning of the background slightly behind the plane of bubbles further improves the shadow separation.

High-resolution KODACHROME-25 TM transparency film is used for best bubble definition.

The finished slide is presented to a BRINKMAN TM particle size analyzer for measurements and calculations. For this purpose, a special slide holder and mounting bracket is provided by another aspect of this invention, which features x- and y-axis controls, so that all portions of a slide may be examined and analyzed. Bubble shadows on transparencies are then counted and measured just as "particles" suspended in liquid or attached to a glass slide would be.

CONCLUSION

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

What I claim is:

1. A bubble measurement cell for measuring size distribution of gas bubbles in a liquid, by isolating said bubbles in situ from a high volume of bubbles without modifying said bubbles in any way, said bubble measurement cell being adapted for insertion in a flotation column having a transparent, vertically-oriented, bubble-viewing window therein, said bubble measurement cell comprising: (a) an antechamber, for placement adjacent to said window in said flotation column, said antechamber (a) being provided with (i) a transparent rear face, said transparent bubble-viewing window and said transparent rear face being provided for the purpose of allowing light to enter in sufficient quantity to illuminate the bubbles and to enable photographic imaging thereof and (ii) a forward, downwardly-pointing deflection wedge to deflect upwardly-moving bubbles; (b) a transparent viewing chamber, said transparent viewing chamber (b) being situated to the rear of said antechamber (a), said transparent viewing chamber (b) including (iii) a rear face, (iv) a transparent front face spaced from said rear face, and (v) a pair of inner, vertical, lateral spacers, said transparent viewing chamber (b) being bounded at its bottom by (vi) a pair of inner, transversely-running, wedges, said wedges thereby providing (vii) a narrow inlet, said narrow inlet leading to (viii) a region of said viewing chamber (b) which is a region of larger cross-sectional area by being thicker and wider than the thickness and the width of said narrow inlet; and (c) means at the upper end of said viewing chamber to permit the escape of gas bubbles; whereby a monolayer of said bubbles is presented in said transparent viewing chamber, thereby to enable the taking of a photograph of the shadows of said bubbles, said photograph being adapted to be subjected to photographic analysis for the measurement of the size the distribution of said bubbles.

2. The bubble measurement cell of claim 1 wherein said photographic analysis is adapted to carry out by the introduction of said photograph to a semi-automated, computerized particle size analyzer having image analysis capabilities, whereby photographic images of shadows of said bubbles are treated as particles by said analyzer, which then generates size and distribution data determined by the shadows of said bubbles.

3. The bubble measurement cell of claim 1 wherein said transparent rear face (i) of said antechamber (a) and said transparent front face (iv) of said viewing chamber (b) are the same face.

4. The bubble measurement cell of claim 1 wherein said narrow inlet (vii) is a rectangular inlet which is adjustable in width.

5. The bubble measurement cell of claim 4 wherein said adjustable width is provided by (ix) a pair of laterally-movable gap adjusters.

6. The bubble measurement cell of claim 1 wherein said viewing chamber (b) is provided with (x) a pair of converging lower edges to provide (xi) a truncated knife edge.

7. The bubble measurement cell of claim 6 wherein said narrow inlet (vii) is situated at the truncated knife edge (xi) and includes (xii) a pair of spaced-apart knife edges.

8. The bubble measurement cell of claim 1 wherein the rear face (iii) of said viewing chamber (b) is provided with (xiii) a white face, said white face being adapted to provide improved contrast for the photographing of the shadows of said bubbles.

9. The bubble measurement cell of claim 1 which includes (xiv) a scale in association with said viewing chamber (b) to enable direct measurement of the size of said gas bubbles by comparison of the photographic image of the shadows of said bubbles with the photographic image of said scale.

10. The bubble measurement cell of claim 1 which includes (xv) a forwardly-projecting frame around said antechamber (a), said frame (xv) including (xvi) a periphery therearound and (xvii) a gasket around said periphery where said periphery contacts said transparent, bubble-viewing window.

11. A method for analyzing the size and the distribution of gas bubbles in a liquid within a vertically-oriented chamber, said method comprising:
providing a vertically-oriented, transparent window in said vertically-oriented chamber to enable the viewing of an upwardly-moving, turbulent stream of gas bubbles;
providing a transparent viewing zone spaced from said transparent window, said transparent viewing zone being situated within said vertically-oriented chamber, said transparent viewing zone also being situated within said upwardly-moving, turbulent stream of gas bubbles;
streaming said gas bubbles upwardly through a narrow rectangular opening into said transparent viewing zone, whereby said gas bubbles are formed into a moving monolayer of bubbles which move upwardly in a laminar flow; and
moving lateral bubbles which are adjacent to said transparent viewing zone laterally away from said transparent viewing zone to separate said bubbles from said previously described monolayer of bubbles which are moving upwardly in a laminar flow, said laterally-moved bubbles being thereby permitted to flow upwardly substantially unimpeded;
whereby there is a minimum of disturbance of said gas bubbles in said transparent viewing zone before and while said bubbles are presented for viewing and photographing; taking a photograph of the shadows of said bubbles; and then analyzing said photograph of said shadows of said bubbles to measure the size and the distribution of said bubbles.

12. The method of claim 11 wherein said analysis of said photograph of said shadows of said bubbles comprises the step of the introduction of said photograph to a semi-automated, computerized particle size analyzer having image analysis capabilities, whereby photographic images of shadows of said bubbles are treated as particles by said analyzer, which then generates size and distribution data determined by the shadows of said bubbles.

13. The method of claim 11 including the step of: passing said upwardly moving stream of gas bubbles through said narrow rectangular opening to said transparent viewing zone, said transparent viewing zone being of larger cross-sectional area; thereby to reduce the likelihood of coalescence, whereby to reduce the adherence of bubbles to said walls of said vertically-oriented chamber and of said transparent viewing chamber, and thereby to enhance bubble shadow definition in a photograph.

14. An attachment for a particle size analyzer, said particle size analyzer including a sample well wherein particles in liquid suspension may be introduced for semi-automatic size distribution analysis, said attachment, comprising: a U-shaped bracket for mounting adjacent said sample well; a photographic slide holder secured to a forward arm of said U-shaped bracket, said slide holder including a pair of downwardly-projecting legs, each said leg being provided with means for holding a photographic slide within said sample well; and means mounted on said forward arm of said U-shaped bracket for permitting both horizontal and vertical movement of said photographic slide.

* * * * *

UNITED STATES PATENT AND TRADEMARK OFFICE
CERTIFICATE OF CORRECTION

PATENT NO. : 5,152,175
DATED : October 6, 1992
INVENTOR(S) : Vaughan G. Reynolds It is certified that error appears in the above-identified patent and that said Letters Patent is hereby corrected as shown below:

<u>COLUMN 8</u>

Line 45, change "BRINKMAN" to --BRINKMANN--

Signed and Sealed this

Twenty-first Day of September, 1993

Attest:

BRUCE LEHMAN

Attesting Officer

Commissioner of Patents and Trademarks